Figure 1:
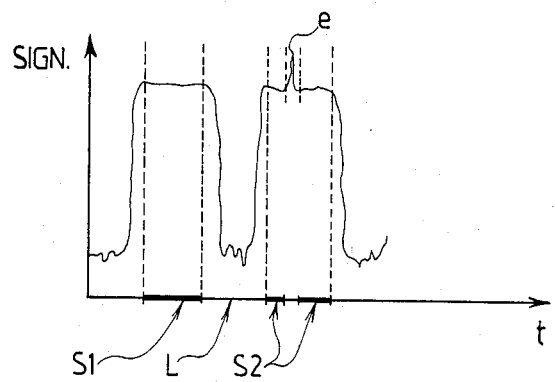

United States Patent [19]

Kimmo et al.

[11] Patent Number: 4,690,900
[45] Date of Patent: Sep. 1, 1987

[54] PROCEDURE FOR PHOTOMETRIC MEASUREMENT OF LIQUIDS IN REACTION VESSELS, AND REACTION VESSEL

[75] Inventors: Käyhkö Kimmo; Kari H. Helenius, both of Espoo, Finland

[73] Assignee: Kone Oy, Helsinki, Finland

[21] Appl. No.: 462,046

[22] Filed: Jan. 28, 1983

[30] Foreign Application Priority Data

Feb. 5, 1982 [FR] France ................................. 820372

[51] Int. Cl.$^4$ ............................................. G01N 21/03
[52] U.S. Cl. ..................................... 436/47; 356/246; 422/65; 422/67; 422/102
[58] Field of Search ..................... 198/460, 690, 648; 250/573, 574, 576; 356/409, 414, 436, 440, 244, 246, 432; 422/63–67, 102, 82, 52; 436/43, 44, 46, 47, 172

[56] References Cited

U.S. PATENT DOCUMENTS

| 1,939,088 | 12/1933 | Styer | 356/436 |
| 2,632,045 | 3/1953 | Sziklai | 422/58 X |
| 3,052,340 | 9/1962 | Lyons et al. | 198/648 X |
| 3,484,170 | 12/1969 | Smythe et al. | 422/82 X |
| 3,660,638 | 5/1972 | Oberli | 422/66 |
| 3,966,323 | 6/1976 | Matsuoka et al. | 356/409 X |
| 3,973,911 | 8/1976 | von Smolinski et al. | 436/172 X |
| 4,003,834 | 1/1977 | Coombs | 422/72 X |
| 4,063,816 | 12/1977 | Itoi et al. | 356/414 X |
| 4,063,817 | 12/1977 | Shimamura et al. | 356/414 X |
| 4,190,146 | 2/1980 | Knuchel | 198/460 |
| 4,195,060 | 3/1980 | Terk | 422/102 X |
| 4,201,478 | 5/1980 | Gerlier et al. | 356/409 X |
| 4,251,159 | 2/1981 | White | 356/246 |
| 4,338,279 | 7/1982 | Orimo et al. | 422/65 X |
| 4,355,712 | 10/1982 | Bruno | 198/460 |
| 4,431,307 | 2/1984 | Suovaniemi | 422/102 X |

FOREIGN PATENT DOCUMENTS 57-208439 12/1982 Japan ................................... 356/246

Primary Examiner—Barry S. Richman
Assistant Examiner—Michael S. Gzybowski
Attorney, Agent, or Firm—Martin Smolowitz

[57] ABSTRACT

A procedure for photometric measurement of liquids in a reaction vessel in an automatic analyser, with a radiation flow having its course perpendicular to a row of the reaction vessel, so as to provide a reliable and positively operating measuring method for the photometric measurement of the liquids. The procedure is characterized in that the radiation flow and the reaction vessel are in movement relative to each other during the measurement. The invention affords the advantage of improved accuracy of measurement and improved reliability since it becomes possible, by measuring a moving object and at the same time calculating the mean of the radiant flux over accepted portions of the signal, to eliminate the error of measurement introduced by a dirt particle or by a scratch. The invention also concerns a row of reaction vessels employed in the procedure, wherein each reaction vessel is contiguous to the next and separated by a wall. The row of reaction vessels is characterized in that the bottom of each reaction vessel consists of a lens focussing luminescence radiation. This affords the advantage that the lens enables a luminiscence measurement to be performed simultaneously with the photometric measurement.

8 Claims, 5 Drawing Figures

U.S. Patent  Sep. 1, 1987  4,690,900

PROCEDURE FOR PHOTOMETRIC MEASUREMENT OF LIQUIDS IN REACTION VESSELS, AND REACTION VESSEL

BACKGROUND OF INVENTION

The present invention concerns a procedure for photometric measurement of liquids in a reaction vessel by means of a radiation flow with a course perpendicular against a row of reaction vessels in an automatic analyser.

In procedures and devices known in the art, for instance, circular reaction vessels resembling test tubes are used, the measurement on the liquid in the reaction vessel being made from their side, perpendicularly to the vessel. The most serious drawback is then the fact that the measuring signal is altered by the circular shape of the tubular reaction vessel, whereby it is possible to obtain an exact reading only at the centre of the vessel. Therefore, mean values cannot be used at all, with the consequence that dirt particles and scratches easily cause errors in the results of measurements. In addition, the procedure is slow, and automation of the sample manipulation is difficult to arrange.

In another procedure known in the art, rows of reaction vessels (so-called cuvettes) are employed, which often have straight measuring surfaces. One makes in that case the measurement on one vessel at a time, directing the radiation flow through the liquid under measurement from one side of the reaction vessel. Dirt particles and scratches on the vessel still constitute a detriment and give rise to measuring errors. Moreover, the procedure is slow and automation of the sample movements is difficult because in the method two directions of movement must be provided for the cuvettes and these have to be synchronized with each other.

SUMMARY OF INVENTION

The object of the present invention is to eliminate the drawbacks mentioned and to provide a reliable and positively operating measuring method for photometric measurement of liquids. The procedure of the invention is characterized in that the radiation flow and the reaction vessel are in motion relative to each other during the photometric measurement of the liquid.

The procedure according to an advantageous embodiment of the invention is characterized in that by means of the radiation flow used for measurement of liquids the distance between reaction vessels and the location of the reaction vessels is also measured. The advantage is hereby gained that no mode or means used need be specifically devised for locating the reaction vessel, and the position fixing need not be synchronized.

The procedure according to another advantageous embodiment is characterized in that of the radiation flow the mean value is measured over the entire useful length of the reaction vessel.

The advantage afforded by the invention is improved accuracy of measurement and reliability due to the circumstance that it is possible, by making the measurement on an object in motion and by calculating at the same time the mean of the radiation flux over accepted portions of the signal, to eliminate the error of measurement caused by a dirt particle or a scratch on the vessel.

The procedure according to yet another advantageous embodiment is characterized in that, in order to move the row of reaction vessels, this row is grasped in one direction of travel by an engagement member. The advantage is now that the moving of the reaction vessel row, or the cuvette, can be made simple. The same engagement member which makes the measurement possible also makes possible the cuvette pick-up operation.

The invention also concerns the reaction vessel row employed in the procedure, in this row each reaction vessel being contiguous to the next, separated by a common wall to form a cuvette. The reaction vessel row according to the invention is characterized in that the bottom of each reaction vessel consists of a lens focussing luminescence radiation. Hereby the advantage is gained that the lens enables a luminescence measurement of the liquid to be carried out simultaneously with the photometric measurement.

The reaction vessel row according to an advantageous embodiment is characterized in that at one end at least of the reaction vessel rows there is a mating member presenting a portion bevelled in the direction in which the engagement member approaches.

The reaction vessel row according to another advantageous embodiment is characterized in that at one end at least of the reaction vessel row there is a mating member carrying a magnet bit or a bit of magnetizable material.

These two embodiments afford the advantage that the engaging member may enter into engagement with a row of reaction vessels by one single movement, in only one direction.

DESCRIPTION OF INVENTION

Figure 3:
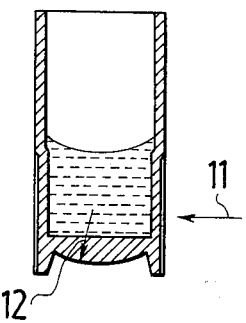
Figure 2:
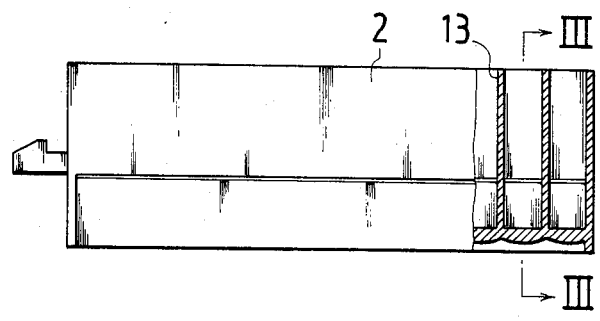
Figure 4:
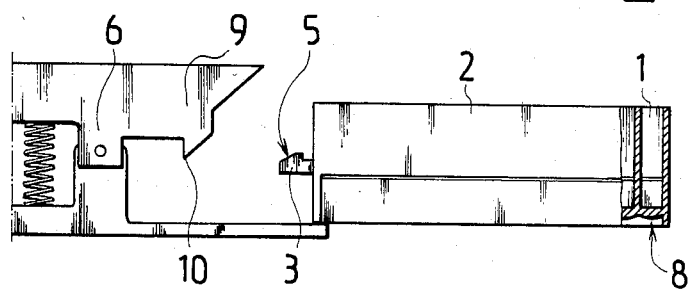
Figure 5:
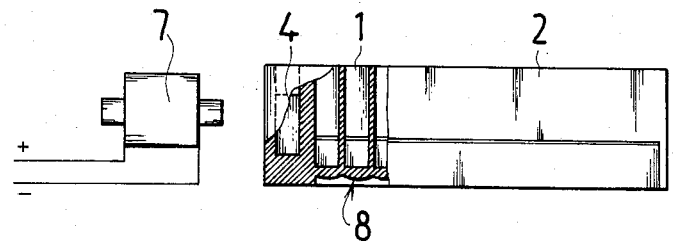

The invention is described in the following in greater detail with the aid of an example by referring to the drawing attached, wherein:

FIG. 1 presents the measuring signal from photometric measurement of liquids in a row of reaction vessels plotted over time, FIG. 2 presents a row of reaction vessels in elevational view and partly sectioned, FIG. 3 shows the cross-section of the reaction vessel sectioned along the line III—III in FIG. 2, and FIGS. 4 and 5 display various modes of engagement between a reaction vessel row and the engagement member.

The procedure is used to measure various liquids photometrically in reaction vessels 1 which constitute a row of reaction vessels 2. The row of reaction vessels, or the cuvette 2, is provided with a mating member 3 or 4, which is grapped by a parallel movement of an engagement member 6 or 7 and the cuvette is transported to a location where it is filled with the liquids to be measured. After an adequate reaction and stabilizing perod for the liquids, the cuvette 2 is moved with the same engagement member past the measuring head of a photometric unit in such a way that the electronic signal response to the measuring radiation flux 11 passing through the liquid and striking the detector will be as shown in FIG. 1. From the response by the detector is elicited by automatic signal analysis the location S1, S2, etc. of each reaction vessel and the effective length of travel S1, S2, etc. used for the measuring of each liquid sample between inner walls 13 of each reaction vessel 1, wherein any portions e of the signal deviating substantially from the average signal level are disregarded, such signal portions being possibly due to scratches on the surfaces of the cuvette, to dirt particles, etc. The mean of the signal calculated from the said effective lengths of travel corresponds to the absorption properties of each quantity of liquid contained in the reaction vessels or cells of the cuvette as closely as possible.

It is possible with the same motion of the cuvette to measure also the luminescent radiation from each liquid quantity directed through the lens 8 having a suitable radius 12 and constituting the bottom of the reaction vessel 1 to a luminescent radiation detector.

To the purpose of automatically moving the linear cuvette 2 in a way making the measuring procedure feasible, the measuring apparatus is provided with the engagement member 6 or 7 which becomes engaged by a single unidirectional motion with a mating member 3 or 4 on the cuvette 2.

The engagement member engages either a suitably shaped projection 3 on the cuvette 2, or of a piece of material 4 capable of being attracted by a magnet. In the former case, the spring-loaded part 9 of the engagement member 6 yields to the bevelled portion 5 of the mating member, until the tip 10 of the engagement member has passed the bevelled face 5 and the spring force locks the cuvette 2 to the engagement member 7. An engagement member operating with magnetic force, consisting of a piece of magnetizable material suitably shaped or of a permanent magnet 4, is gripped with a permanent or electromagnetic engagement member 7.

It is obvious to a person skilled in the art that the invention is not exclusively confined to the embodiment described in the foregoing and that it may vary within the scope of the claims stated below.

We claim:

1. A procedure for photometric measurement of liquids contained in reaction vessels in an automatic analyzer by utilizing a radiation flow along a path substantially perpendicular to a row of the reaction vessels, comprising:

filling each reaction vessel in a row of vessels with liquid to be photometrically measured, each vessel being contiguous with an adjacent vessel and separated by a common wall so as to form a unitary cuvette;

continuously moving the cuvette and contained liquid past a radiation flux source and a photometric detector measuring unit by engaging a mating member provided at one end of the cuvette with an engagement member in an automatic analyzer capable of moving the cuvette continuously in a longitudinal direction, wherein the reaction vessels are each in continuous movement relative to the photometric detector; and passing the radiation flow continuously through side walls of each reaction vessel and the liquid contained therein and continuously photometrically measuring the contained liquid and also measuring the distance between adjacent reaction vessels, and determining a mean value of the radiation response from signals generated by the photometric measuring unit, so that the mean value of the radiation response is measured over substantially the entire length of each reaction vessel of the cuvette.

2. A photometric measurement procedure according to claim 1, wherein any portion of the photometric measurement signals deviating substantially from an average signal level is disregarded for determining a mean value of the radiation response from each contained liquid.

3. A photometric measuring procedure according to claim 1, wherein luminescence from the liquid in each said reaction vessel of the cuvette is additionally measured through a convex shaped lens which lens comprises a bottom of each reaction vessel.

4. A row of reaction vessels for continuous photometric measurement of liquids, each reaction vessel in the row being contiguous with an adjacent vessel and separated by a common wall so as to form a unitary cuvette, wherein opposite sides of each reaction vessel are flat for receiving a continuous radiation flow from a radiation source, and the bottom of each reaction vessel of the cuvette comprises a lens, said lens having a convex shaped radius on its lower side for directing luminescent radiation from a liquid in the vessel; and at least one end of the cuvette being provided with a mating member adapted for being engaged with an engagement member for use in moving the cuvette continuously past a radiation source by means of the engagement member.

5. A row of reaction vessels according to claim 4, wherein the mating member comprises a projection having a bevelled face which is bevelled upwardly towards the cuvette whereby an engagement member can engage the projection and move the row of reaction vessels continuously past the radiation source.

6. A row of reaction vessels according to claim 4, wherein the mating member comprises a piece of magnetic material for contact by a magnetic engagement member for moving the row of reaction vessels continuously past the radiation source.

7. A procedure for photometric measurement of liquids contained in adjacent reaction vessels in an automatic analyzer by utilizing a radiation flow along a path substantially perpendicular to a row of the reaction vessels, comprising:
   (a) filling each reaction vessel in the row of vessels with a liquid to be photometrically measured, each reaction vessel being contiguous with an adjacent vessel and separated by a common wall so as to form a unitary cuvette;
   (b) continuously moving the cuvette and liquid contained in the vessels past a radiation flux source and a photometric detector measuring unit by engaging a mating member provided at one end of the cuvette with an engagement member in an automatic analyzer capable of moving the cuvette continuously in a longitudinal direction, wherein the reaction vessels are each in continuous movement relative to the photometric detector, and passing the radiation flow continuously through side walls of the reaction vessels and liquid contained therein and continuously measuring the radiation response from signals received by the photometric detector measuring unit;
   (c) continuously measuring the distance between adjacent reaction vessels and determining a mean value of the radiation response for each liquid sample in each reaction vessel over a length of the vessel by disregarding any portion of the measurement signal deviating substantially from an average signal level for determining the mean value of the radiation response from the contained liquid, so that the radiation is measured over substantially the entire length of each vessel; and
   (d) continuously measuring luminescence from the liquid sample in each said reaction vessel through a lens located at a bottom end of each reaction vessel.

8. A row of reaction vessels for making continuous photometric measurements of liquids, each reaction vessel in the row being contiguous with an adjacent vessel and separated by a common wall so as to form a unitary cuvette, wherein opposite sides of each reaction vessel are flat for receiving a continuous radiation flow from a radiation source, and the bottom of each reaction vessel of the cuvette comprises a lens for focusing luminescent radiation from liquid in the vessel, said lens having a convex shaped radius on its lower side for directing luminescent radiation from the liquid in the vessel; and wherein at one end of said row of vessels there is provided a mating member having a bevelled face bevelled upwardly towards the the cuvette and for engaging and moving the vessel row continuously past the radiation source by an engagement member.

* * * * *